United States Patent [19]

Von Witzleben

[11] Patent Number: 5,370,636

[45] Date of Patent: Dec. 6, 1994

[54] PLUG-TYPE CONNECTOR FOR PRODUCING AND INTERRUPTING A LIQUID FLOW CONNECTION

[75] Inventor: Dietrich Von Witzleben, Bremen, Germany

[73] Assignee: Siemens Aktiengesellschaft, Munich, Germany

[21] Appl. No.: 111,572

[22] Filed: Aug. 25, 1993

[30] Foreign Application Priority Data

Aug. 28, 1992 [EP] European Pat. Off. ........ 92114796.3

[51] Int. Cl.⁵ .................................. A61M 25/00
[52] U.S. Cl. ...................... 604/283; 604/88; 604/905; 251/149.8
[58] Field of Search ............ 251/149.1, 149.8; 604/86–91, 905, 244, 246, 280, 283

[56] References Cited

U.S. PATENT DOCUMENTS

| | | |
|---|---|---|
| 2,726,656 | 12/1955 | Lockhart . |
| 3,986,508 | 10/1976 | Barrington . |
| 3,995,630 | 12/1976 | van de Veerdonk ............ 604/88 |
| 4,014,330 | 3/1977 | Denese ............................. 604/88 |
| 4,060,082 | 11/1977 | Lindberg ......................... 604/89 |
| 4,334,536 | 6/1982 | Pfleger ............................ 604/244 |
| 4,861,335 | 8/1989 | Reynolds ......................... 604/88 |
| 4,950,260 | 8/1990 | Bonaldo . |
| 5,065,783 | 11/1991 | Ogle, II . |
| 5,122,123 | 6/1992 | Vaillancourt ................... 604/283 |

FOREIGN PATENT DOCUMENTS

| | | |
|---|---|---|
| 3605664 | 8/1987 | Germany . |
| 8302060 | 6/1983 | WIPO ............................... 604/905 |

*Primary Examiner*—C. Fred Rosenbaum
*Assistant Examiner*—Chalin Smith
*Attorney, Agent, or Firm*—Hill, Steadman & Simpson

[57] ABSTRACT

In a plug-type connector having two plug parts for producing and interrupting a flow connection, in order to enable sealing of the flow branches of the respective parts when separated from one another when the flow connection is interrupted, each plug part is terminated with a perforable septum with a cannula held so as to be longitudinally displaceable in one septum. The cannula and the septa are fashioned with reference to one another such that the septum holding the cannula offers lower resistance to the cannula upon penetration than does the other septum. This results in the cannula first penetrating the septum that holds it when the plug parts are joined and subsequently penetrating the other septum. When releasing the plug parts from one another, the cannula is first withdrawn from the septum that holds it and is then withdrawn from the other septum.

11 Claims, 3 Drawing Sheets

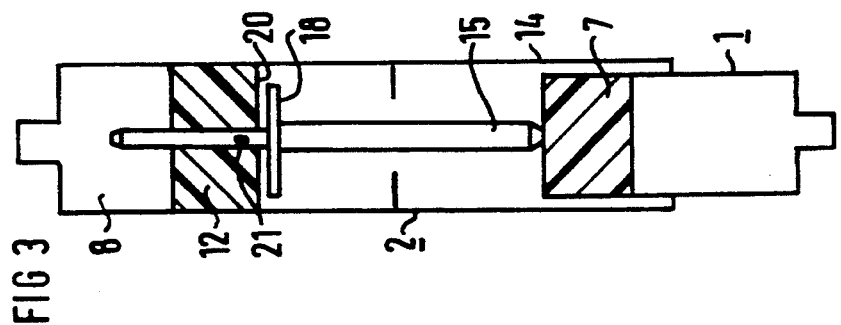
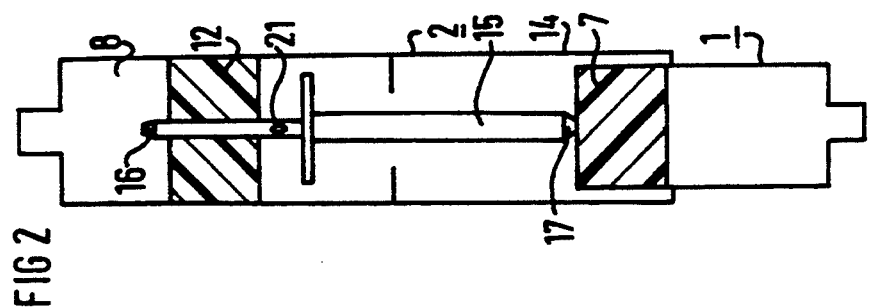
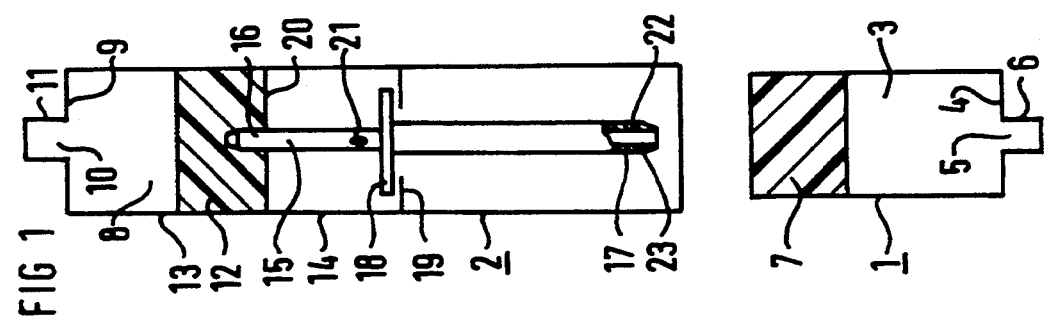

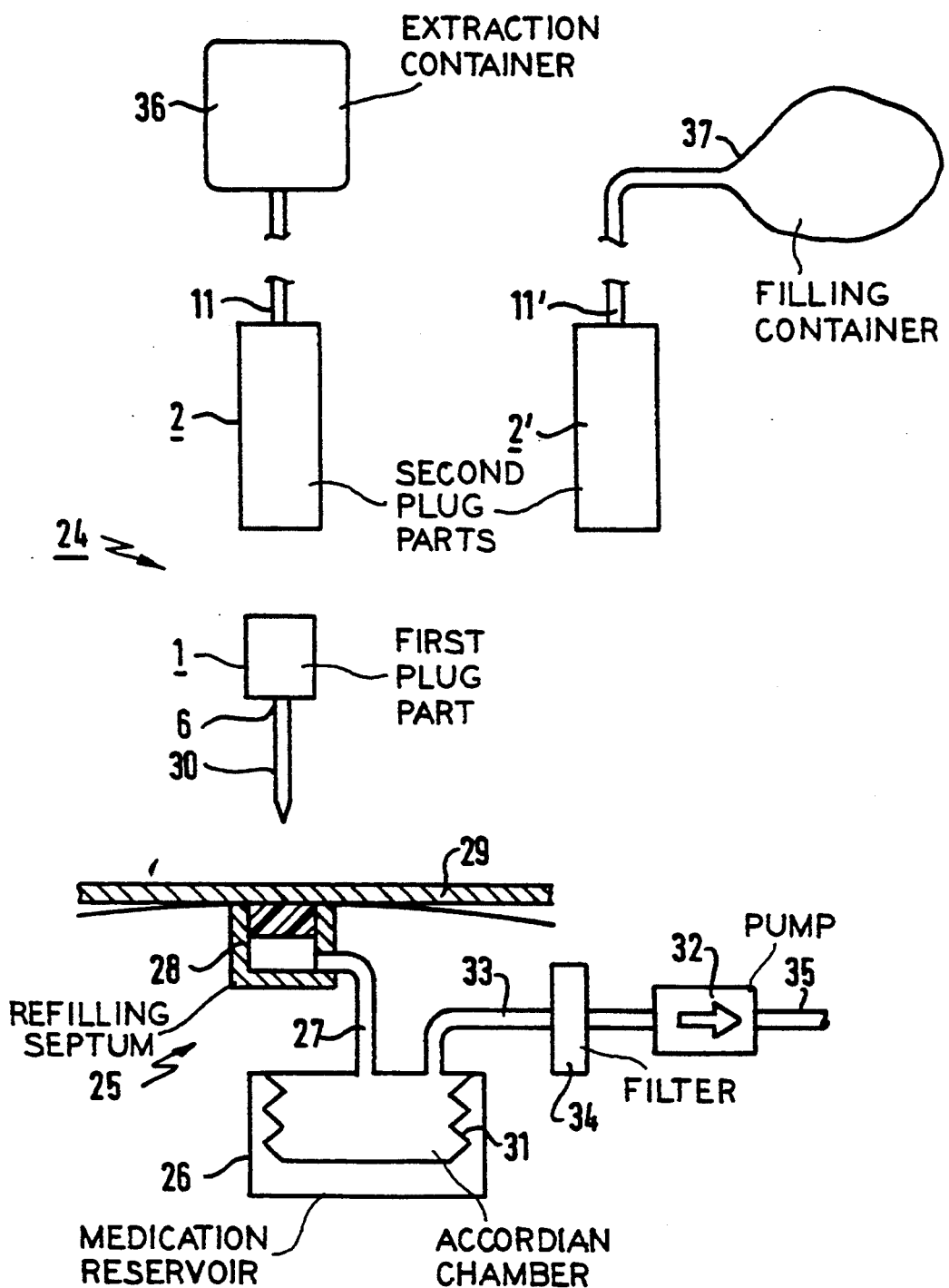

PLUG-TYPE CONNECTOR FOR PRODUCING AND INTERRUPTING A LIQUID FLOW CONNECTION

BACKGROUND OF THE INVENTION

1. Field of the Invention

The present invention is directed to a plug-type connector for producing and interrupting a fluid flow connection, particularly in a medical apparatus such as an implantable infusion pump.

2. Description of the Prior Art

Plug-type connectors for joining two components through which a liquid flow is to arise are known which block a one-way flow of liquid until the components are joined. For this purpose, a first plug part has a flow passage terminated at one side by a perforable septum, and a second plug part contains a flow channel terminated by a stopper with a cannula arranged therein. Means are provided for the detachable connection of the two plug parts, whereby the perforable septum is arranged in the first plug part and the cannula is arranged in the second plug part so that the cannula penetrates the perforable septum when the plug parts are joined and produces a flow connection between the flow passage and the flow channel.

In such a plug-type connector disclosed in U.S. Pat. No. 4,950,260, the first of two plug parts a liquid entry port terminated by a perforable septum, whereas the second plug part has a cannula connected to a liquid outlet, this cannula being rigidly held in a stopper and being firmly surrounded by a sleeve. When the two plug parts are joined, the cannula penetrates the perforable septum and thus produces a liquid passage between the liquid entry port and the liquid outlet. The sleeve of the second plug part serves to center the two plug parts when they are joined. The sleeve also protects the cannula when the two plug parts are separated from one another. Since only the first plug part in this known plug-type connector is provided with a sealing means in the form of the perforable septum, this known plug-type connector can only be employed when the liquid transfer (flow) is to ensue in a single direction, namely from the first to the second plug part.

SUMMARY OF THE INVENTION

It is an object of the present invention to provide a plug-type connector which when the plug parts are decoupled, enables a reliable sealing of the two flow branches separated from one another independently of the flow direction.

This object is achieved in accordance with the principles of the present invention in a plug-type connector of the type initially cited wherein the stopper in which the cannula is held in the second plug part is formed by a second perforable septum in which the cannula can be displaced in the direction of its longitudinal axis. The cannula and the perforable septa are fashioned with reference to one another such that the second perforable septum presents less mechanical resistance to passage of the cannula than does the first perforable septum. The second plug part has detents for limiting the displacement of the cannula in the second plug part between a first and a second position, whereby the cannula only partially penetrates the second perforable septum in the first position and completely penetrates it in the second position. The length of the cannula is dimensioned such that, in its second position, it also completely penetrates the first perforable septum when the plug parts are joined.

When joining the two plug parts, the cannula is first pressed by the perforable septum of the first plug part through the second perforable septum in the second plug part before the cannula also penetrates the first perforable septum in the first plug part. Conversely, when the two plug parts are released from one another, the cannula is first withdrawn from the second perforable septum of the second plug part to such an extent that the second perforable septum automatically closes; only then is the first perforable septum of the first plug part pulled off of the cannula. It is assured in this way that both plug parts are always sealed toward the outside, so that, for example, external air cannot penetrate into the flow paths of the plug-type connector either when producing or when decoupling the plug connection.

In order that the cannula first penetrates the second perforable septum in the second plug part when the plug parts are joined, or is withdrawn from this septum first when the plug connection is decoupled, preferably the perforable septa have different coefficients of friction vis-a-vis the cannula penetrating them, as a consequence of different material properties. This can be achieved by different types of material or different densities of the same material. Alternatively or in addition thereto, the cannula may exhibit respectively different coefficients of friction vis-a-vis the perforable septa as a consequence of a different shape and/or surface quality at its two ends. Thus, for example, the end of the cannula lying in the second perforable septum can be fashioned more pointed than the other end in order to thus more easily penetrate the second perforable septum.

In an embodiment of the plug-type connector of the invention, the tip of the cannula that penetrates the first perforable septum has an opening having an edge that proceeds perpendicularly relative to the longitudinal axis of the cannula. This results in the perforable septum of the first plug part coming to lie against the edge of the opening in sealing fashion when the two plug parts are joined and prevents external air from flowing into the cannula when the cannula penetrates the second perforable septum in the second plug part and thus produces a connection to the interior thereof.

In a preferred embodiment of the plug-type connector of the invention, the second plug part is in the form of a sleeve that is open at one end and is closed at the other end by the stopper/septum with the cannula projecting into the interior of the sleeve, with the sleeve surrounding the exterior of the first plug part in sealing fashion when the two plug parts are joined. The length of the sleeve is thereby dimensioned such that the two plug parts engage into one another in sealing fashion when they are joined before the cannula penetrates the second perforable septum in the second plug part. It is assured in this way that external air can not penetrate into the interior of the second plug part, which is important, for example, if the perforable septum of the first plug part—due to an operating error—does not correctly press in sealing fashion against the opening of the cannula.

It is particularly advantageous in this context when the cannula has a lateral opening that is arranged in the direction of the longitudinal axis of the cannula so that it lies in the inside of the sleeve in the first position of the cannula and is surrounded in sealing fashion by the second perforable septum in the second position.

The plug-type connector of the invention proves particularly advantageous in conjunction with the filling or refilling of liquid medications in implantable medication dosing devices. Known, implantable medication dosing devices (German OS 36 05 664), for example for insulin, cytostatics or pain killers, include a medication reservoir that must be refilled at defined chronological intervals that are dependent on the specific needs of the patient for medication. This refilling usually ensues transcutaneously with an injection syringe whose cannula is pierced through the skin and through a refilling septum lying therebelow that seals the medication reservoir from the exterior. In order to be able to first suction out medication residues from the medication reservoir before a refilling thereof, it is provided in an embodiment of the invention that the first plug part is connected to the liquid reservoir to be emptied and an extraction container having an interior chamber at a lower pressure than prevails in the liquid reservoir is connected to the second plug part. As soon as the plug connection is produced between the two plug pans, the liquid residues are suctioned out of the liquid reservoir into the extraction container. When the two plug parts are again separated from one another, the liquid reservoir as well as the extraction container are respectively sealed from the outside.

For refilling the liquid reservoir, the first plug part is connected to the liquid reservoir to be filled and a liquid-filled filling container having an interior chamber at a higher pressure than prevails in the liquid reservoir is connected to the second plug part.

In conjunction with the transcutaneous filling or refilling of liquid medications in implantable medication dosing devices, a cannula for piercing a refilling septum that seals the liquid reservoir from the exterior can be connected to the first plug part. A reliable refilling is thereby enabled, whereby the risk of the cannula breaking off, bending off or slipping out of the puncture location and, connected therewith, the risk of mis-injections, are particularly avoided.

DESCRIPTION OF THE DRAWINGS

FIGS. 1–5 respectively show stages in a sequence for coupling the two plug parts in a connector constructed in accordance with the principles of the present invention.

FIG. 8 schematically illustrates exemplary embodiment of the plug-connector of the invention for emptying and refilling an implanted medication dosing device.

DESCRIPTION OF THE PREFERRED EMBODIMENTS

Figure 7:
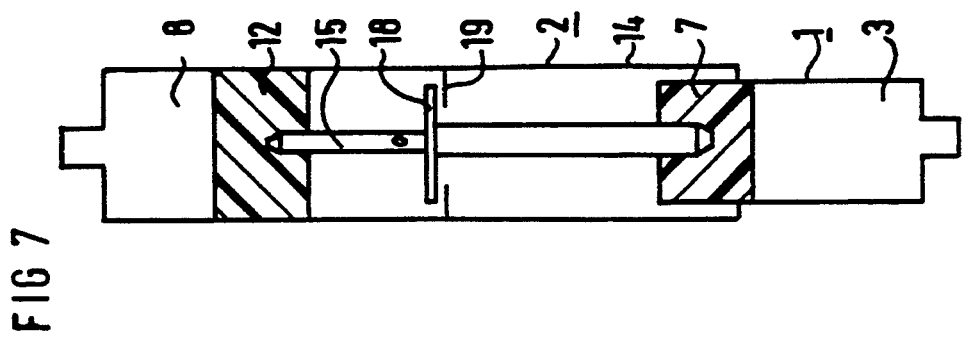
FIGS. 6 and 7 respectively show stages in a sequence as the two plug parts of FIGS. 1–5 are withdrawn.

FIGS. 1 through 7 respectively show longitudinal sectional view of a plug-connector composed of a first plug part 1 and of a second plug part 2 in successive phases when joining and subsequently decoupling the two plug parts 1 and 2. The first plug part 1 contains a flow passage 3 in the form of a chamber having an opening 5 for the passage of a flow medium in the region of the base 4 of the chamber. The region of the opening 5 of the plug part 1 is provided with a connecting part 6 for connecting a catheter (not shown) for the flow agent. The open side of the chamber 3 lying thereopposite is closed by a perforable septum 7.

The second plug part 2 contains a flow channel 8—likewise in the form of a chamber—that contains an opening 10 in the region of the base 9 of the chamber for the passage of the flow agent and that is likewise provided with a connecting part 11 for connection of a catheter for the flow agent. At its opposite side, the chamber 8 is sealed by a stopper 12 in the form of a second perforable septum which, as the first perforable septum 7, is preferably composed of bromobutyl rubber. The wall 13 of the chamber 8 is lengthened proceeding beyond the second perforable septum 12 to form a sleeve 14 whose inside clearance essentially corresponds to the outside clearance of the first plug part 1, so that the sleeve 14 surrounds the first plug part 1 in sealing fashion at its exterior when the two plug parts 1 and 2 are joined.

Figure 5:
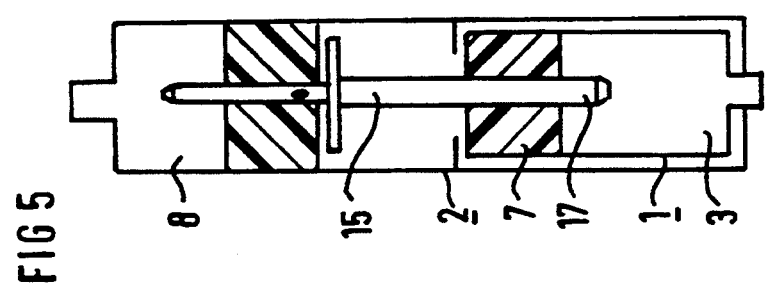
Figure 4:
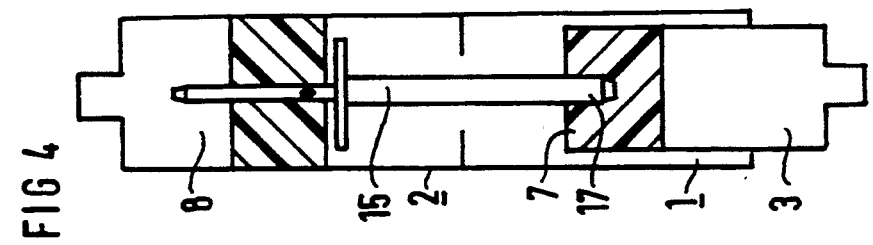

The second perforable septum 12 serves as a holder for a cannula 15 that extends in the inside of the sleeve 14 in a longitudinal direction relative thereto, and which has an end 16 plugged into the second perforable septum 12. The other end 17 of the cannula 15 lies in the region of the opening of the sleeve 14. The cannula 15 is displaceable in the septum 12 in the direction of its longitudinal axis, causing it to penetrate the perforable septum 12 to a greater or lesser extent. The cannula 15 has a shoulder 18 (which may be annular) which limits its motion between two detents 19 and 20 of the second plug part 2. The detents 19 and 20 are arranged such that the second perforable septum 15 is only partially penetrated by the end 16 of the cannula 15 in a first position—shown in FIGS. 1 and 7—wherein the shoulder 18 of the cannula 15 is pressing against the detent 19, so that the cannula 15 is sealed in this position. When the shoulder 18 of the cannula 15 lies against the second detent 20 (which in the illustrated embodiment is formed by the second perforable septum 12) in the position shown in FIGS. 3, 4 and 5, the second perforable septum 12 is completely penetrated by the cannula 15, so that a connection to the interior of the chamber 8 exists via the cannula 15. The cannula 15 also has a lateral opening 21 arranged in the direction of the longitudinal axis of the cannula 15 so that it lies in the inside of the sleeve in the first position (FIGS. 1 and 7) and is surrounded in sealing fashion by the second perforable septum 12 in the second position (FIGS. 3, 4 and 5).

The length of the sleeve 14 is dimensioned such that it projects beyond the tip 17 of the cannula 15 in the first position (FIGS. 1 and 7) of the cannula 15, so that this is largely protected against possible damage due to improper handling. Further, the first plug part 1 when joining the plug parts 1 and 2 is maintained in a fixed lateral position relative to the cannula 15 as a result thereof before the cannula 15 strikes the perforable septum 7 with its tip 17.

The two perforable septa 7 and 8 and the cannula 15 are fashioned with reference to one another such that the second perforable septum 12 presents lower resistance to the cannula 15 upon penetration than does the first perforable septum 7. This can be achieved in various ways in that, for example, the two perforable septa 7 and 12 have respectively different coefficients of friction vie-a-vie the cannula 15 that penetrates them due to different types of material or densities of material. Alternatively or additionally thereto, the cannula 15 can have respectively different coefficients of friction relative to the perforable septa 7 and 12 due to different shapes and/or surface qualities at its two ends 16 and 17. Thus, for example, the cannula 15 can have a smaller outside diameter and a smoother surface at its end 16 lying in the second perforable septum 12 than at the other end 17. As FIG. 1 shows, the opening 22 of the cannula 15 at its tip 17 penetrating the first perforable septum 7 is provided with an opening edge 23 that proceeds perpendicularly relative to the longitudinal axis of the cannula 15, so that the first perforable septum 7 first presses against the opening 22 in sealing fashion when the two plug parts 1 and 2 are joined (FIGS. 2 and 3).

FIG. 1 shows the plug-type connector when the plug parts 1 and 2 are completely decoupled from one another.

As FIG. 2 shows, the first plug part 1 is first centered by the sleeve 14 relative to the cannula 15 when the two plug parts 1 and 2 are joined. At the same time, the inside of the sleeve 14 is sealed from the outside by the plug part 1. As the joining of the two plug parts 1 and 2 is continued, the first perforable septum 7 presses against the tip 17 of the cannula 15 in sealing fashion and presses the other end 16 thereof through the second perforable septum 12. When the cannula 15 has just penetrated the second perforable septum 12, the lateral opening 21 of the cannula 15 is still situated in the inside of the sleeve 14, so that the opening 21 is in communication via the cannula 15 with the flow channel 8 of the second plug part 2 and can be suctioned empty.

According to the illustration in FIG. 3, the cannula 15 is pressed through the second perforable septum 12 by the first perforable septum 7 given continued joining motion of the two plug parts 1 and 2 until the shoulder 18 lies against the detent 20 formed by the second perforable septum 12. In this position of the cannula 15, the lateral opening 21 thereof is surrounded in sealing fashion by the second perforable septum 12, so that there is no longer any connection between the flow channel 8 and the interior of the sleeve 14.

As FIGS. 4 and 5 show, given continued joining motion of the two plug parts 1 and 2, the end 17 of the cannula 15 is pressed into the perforable septum 7 of the first plug part 1 until the cannula 15 completely penetrates the first perforable septum 7 and produces a flow connection between the flow passage 3 of the first plug part 1 and the flow channel 8 of the second plug part 2.

Figure 6:
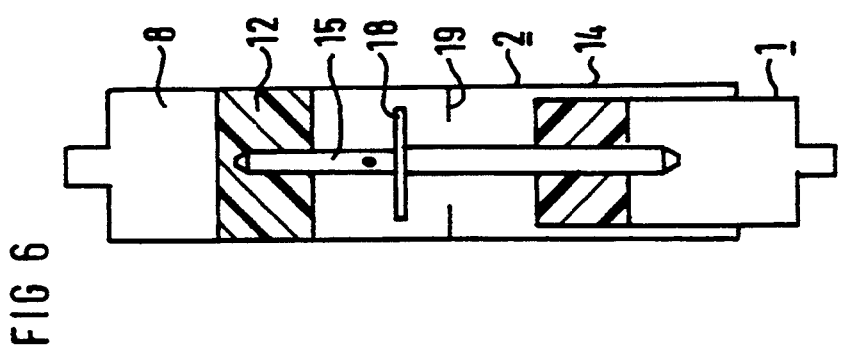

When decoupling the two plug parts 1 and 2, the cannula 15, according to FIG. 6, is first withdrawn from the perforable septum 12 of the second plug part 2 until the shoulder 18 of the cannula 15 comes to lie against the detent 19. In this position of the cannula 15, the flow channel 8 of the second plug part 2 is sealed relative to the inside of the cannula 15 and the sleeve 14 by the self-healing perforable septum 12.

As FIG. 7 shows, the cannula 15 is also withdrawn from the perforable septum 7 of the first plug part given continued removal of the two plug parts 1 and 2 from one another, whereby the perforable septum 7 seals the flow passage 3 toward the outside.

The plug-type connector of the invention is thus extremely simple to manipulate, and it is assured that both plug parts 1 and 2 are also sealed from the outside, so that, for example, outside air cannot penetrate into the flow paths of the plug-type connector either when producing or when releasing the plug connection.

FIG. 8 shows a further exemplary embodiment of the plug-type connector 24 of the invention in conjunction with the refilling of liquid medications into an implantable medication dosing device 25. Given the implanted medication dosing device 25 (shown only partially and in simplified fashion), a medication reservoir 26 is connected via a filling catheter 27 to a refilling septum 28 that is arranged under the skin 29 of a patient such that a liquid medication such as, for example, insulin can be filled with a cannula 30 through the refilling septum 28 in to an accordion chamber 31 of the medication reservoir 26 after the latter has been emptied. A medication dosing pump 32 withdraws the stored medication by suction from the chamber 31 in dosed portions via a connecting catheter 13, if necessary through a filter 34, and conducts these dosed portions to a catheter 35 that conveys the medication portions to a suitable location in the body of the patient, at which location the doses are administered. The cannula 30, as a component of the first plug part 1, is connected to the connecting part 6 thereof. Two second plug parts 2 and 2' are provided respectively for the emptying and refilling of the medication reservoir 26. The second plug part 2 is connected to an extraction container 36 at its connecting part 11, a lower pressure than in the medication reservoir 26 prevailing in the interior of this extraction container 36. The connecting part 11' of the second plug part 2' is connected to a filling container 37 that contains the medication to be replenished.

The emptying and refilling of the medication reservoir 26 occurs in such a way that the skin 29 and the refilling septum 28 situated therebelow are first pierced with the cannula 30 of the first plug part and access to the medication reservoir 26 is thus created. For extracting residual liquids in the medication reservoir 26, the second plug part 2 is first put in place on the first plug part 1, so that the entire arrangement is evacuated due to the under-pressure in the extraction container 36 and the remaining volume of the medication is removed from the medication reservoir 26, and thereby causing the membrane accordion chamber 31 to contract. Subsequently, the second plug part 2 is withdrawn from the first plug part 1, whereby the perforable septum 7 (see FIGS. 1 through 6) guarantees that the under-pressure is maintained in the arrangement.

For refilling the medication reservoir 26, the plug part referenced 2' is put in place on the first plug part 1, whereby the fresh medication contained in the filling container 37 is sucked in to the medication reservoir 26 due to the under-pressure prevailing in the arrangement until a pressure equalization occurs after complete filling. As already set forth with reference to FIGS. 1 through 7, it is always assured both when emptying as well as when refilling the medication reservoir 26 that no outside air can penetrate into the medication dosing device 25.

Although modifications and changes may be suggested by those skilled in the art, it is the intention of the inventor to embody within the patent warranted hereon all changes and modifications as reasonably and properly come within the scope of his contribution to the art.

I claim as my invention:

1. A plug-type connector for producing and interrupting a liquid flow connection comprising:
a first plug part having a first flow passage terminated at one side by a first perforable septum;
a second plug part having a second flow passage terminated by a second perforable septum, and having a cannula with a longitudinal axis held in said second perforable septum and displaceable in said second perforable septum in the direction of said longitudinal axis;
means for releasably connecting said first and second plug parts;

said cannula, said first perforable septum and said second perforable septum having respective coefficients of friction so that said second perforable septum presents lower resistance to penetration by said cannula than said first perforable septum;

said second plug part having first and second detents spaced from each other and engageable with said cannula for limiting displacement of said cannula in said second plug part between a first position wherein said cannula only partially penetrates said second perforable septum and a second position wherein said cannula completely penetrates said second perforable septum; and said cannula having a length along said longitudinal axis so that said cannula completely penetrates said first perforable septum in said second position to produce a flow connection between said first and second flow passages.

2. A plug-type connector as claimed in claim 1 wherein said first and second perforable septa have respectively different material properties for producing said respectively different coefficients of friction relative to said cannula.

3. A plug-type connector as claimed in claim 1 wherein said cannula has a first end which penetrates said first perforable septum and a second end which penetrates said second perforable septum, and wherein said first and second ends have respectively different shapes for creating said respectively different coefficients of friction.

4. A plug-type connector as claimed in claim 1 wherein said cannula has a first end which penetrates said first perforable septum and a second end which penetrates said second perforable septum, and wherein said first and second ends have respectively different surface qualities for creating said respectively different coefficients of friction.

5. A plug-type connector as claimed in claim 1 wherein said cannula has a tip which penetrates said first perforable septum, said tip having an opening therein with an opening edge extending perpendicularly relative to said longitudinal axis.

6. A plug-type connector as claimed in claim 1 wherein said second plug part further comprises a sleeve closed at one end by said second perforable septum and open at an opposite end, with said cannula projecting into an interior of said sleeve, and wherein said first plug part has an exterior surface having dimensions so that said sleeve surrounds said exterior surface of said first plug part for sealing said first and second plug parts when said first and second plug parts are connected.

7. A plug-type connector as claimed in claim 6 wherein said cannula has an opening disposed laterally relative to said longitudinal axis, said opening disposed along said longitudinal axis at a location so that said opening is disposed inside said sleeve in said first position and is surrounded and sealed by said second perforable septum in said second position.

8. A plug-type connector as claimed in claim 1 for use with a liquid reservoir, and further comprising:
extraction container means, connected to said flow passage of said second plug part, for emptying liquid from said liquid reservoir and having an interior pressure which is lower than an interior pressure of said liquid reservoir.

9. A plug-type connector as claimed in claim 8 wherein said liquid reservoir has a refilling septum, and said plug-type connector further comprising a cannula connected to said flow passage of said first plug part for piercing said refilling septum.

10. A plug-type connector as claimed in claim 1 for use with a liquid reservoir, and further comprising:
filling container means, connected to said flow passage of said second plug part, containing liquid for filling said liquid reservoir and having an interior pressure which is higher than an interior pressure of said liquid reservoir.

11. A plug-type connector as claimed in claim 10 wherein said liquid reservoir has a refilling septum, and said plug-type connector further comprising a cannula connected to said flow passage of said first plug part for piercing said refilling septum.

* * * * *